United States Patent
Lieber

(10) Patent No.: US 6,852,111 B1
(45) Date of Patent: Feb. 8, 2005

(54) LAPAROSCOPIC ELECTROTOME

(76) Inventor: David Lieber, 1924 Bruns Lane Ct., Springfield, IL (US) 62702

( * ) Notice: Subject to any disclaimer, the term of this patent is extended or adjusted under 35 U.S.C. 154(b) by 182 days.

(21) Appl. No.: 10/371,503

(22) Filed: Feb. 21, 2003

Related U.S. Application Data

(60) Provisional application No. 60/371,557, filed on Apr. 11, 2002.

(51) Int. Cl.[7] .............................................. A61B 18/18
(52) U.S. Cl. ........................................ 606/47; 606/113
(58) Field of Search .............................. 606/47–50, 113

(56) References Cited

U.S. PATENT DOCUMENTS

| | | | |
|---|---|---|---|
| 4,060,087 A | 11/1977 | Hiltebrandt | |
| 4,362,160 A | 12/1982 | Hiltebrandt | |
| 5,035,696 A | * 7/1991 | Rydell | 606/47 |
| 5,133,713 A | 7/1992 | Huang | |
| 5,437,665 A | 8/1995 | Munro | |
| 5,611,803 A | 3/1997 | Heaven | |
| 5,810,807 A | * 9/1998 | Ganz et al. | 606/47 |
| 5,971,994 A | 10/1999 | Fritzsch | |
| 6,123,665 A | * 9/2000 | Kawano | 600/104 |
| 6,416,513 B1 | 7/2002 | Dresden | |
| 6,616,659 B1 | * 9/2003 | de la Torre et al. | 606/47 |
| 6,659,105 B2 | * 12/2003 | Burbank et al. | 128/898 |

* cited by examiner

*Primary Examiner*—Michael Peffley
(74) *Attorney, Agent, or Firm*—William S. Ramsey

(57) ABSTRACT

This electrotome is designed for insertion through a trocar into a body cavity for laproscopic surgery, in particular, for resection of diseased tissue. The instrument comprises three coaxial components, a core rod, tubular conductor, and outer sheath, each with a handle, and a ribbon like cutting electrode. The cutting electrode is retained flat against the core rod for insertion and manipulation of the instrument adjacent to the tissue to be resected, and the electrode is extended into a bow for cutting. After extension and electrical heating, the electrotome is rotated in a clockwise or counterclockwise manner with simultaneous resection and cauterization of the tissue. The excised tissue can then be trapped between the electrode and core rod for removal from the body cavity.

15 Claims, 4 Drawing Sheets

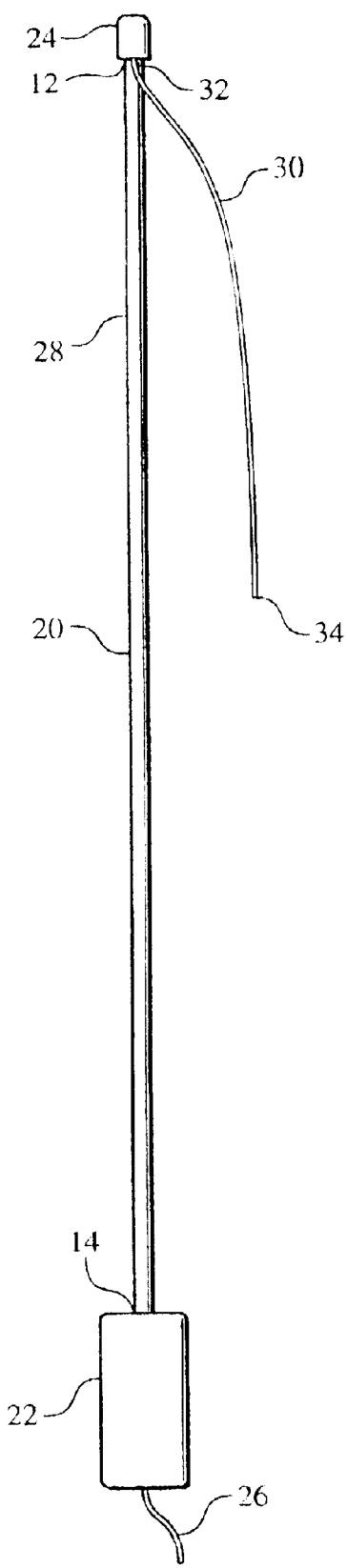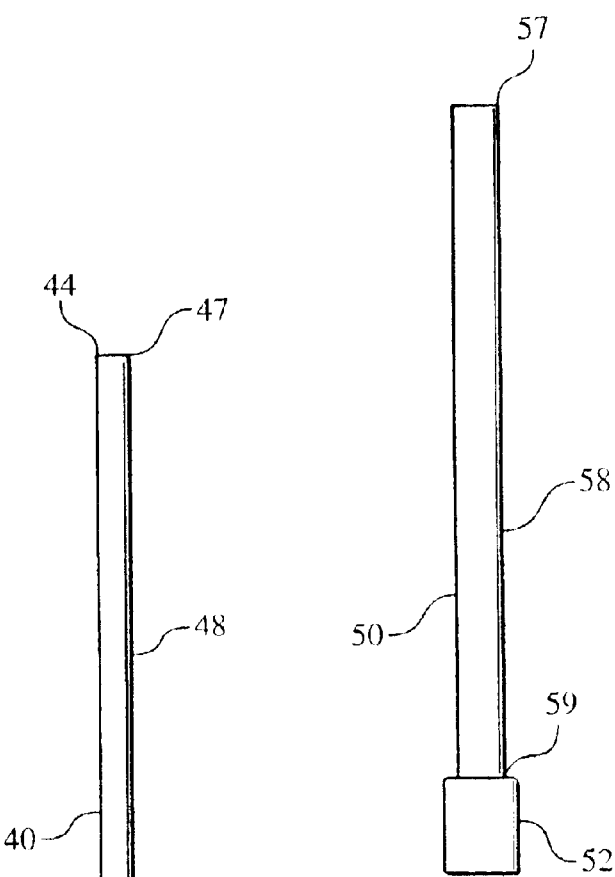
FIG. 3
FIG. 4
FIG. 5

LAPAROSCOPIC ELECTROTOME

CROSS-REFERENCE TO RELATED APPLICATIONS

This application claims priority from U.S. provisional patent application No. 60/371,557, filed Apr. 11, 2002.

STATEMENT REGARDING FEDERALLY SPONSORED RESEARCH OR DEVELOPMENT

Not Applicable.

Reference to a "Microfiche appendix."

Not Applicable.

BACKGROUND OF THE INVENTION

1. Field of the Invention

This application relates to electrical cutting devices for use in laparoscopic surgery.

2. Description of Related Art Including Information Disclosed Under 37 CFR 1.97 and 37 CFR 1.98.

This invention provides an electrotome which is inserted transcutaneously through a standard laparoscopic port or trocar. The electrotome cuts by rotating a heated electrical loop. The size of the loop is adjusted by the user to control the depth of the cut, as, for example, for resection of renal adenomas. The electrotome also is used to grasp the resected tissue for removal through the trocar for pathological examination.

U.S. Pat. No. 4,060,087 discloses a TIF resectoscope in which HF current is applied to two parallel semi-circular loop electrodes. One electrode is neutral and one live. This improvement avoids the use of a single live electrode cutter with the patient grounded, an arrangement sometimes causes burns in the urethra due to capacitive discharge. The working element is thrust forward and electrical current is applied as it retracts back to itself, thereby cutting a groove in the tissue. This process is repeated with the cutting of multiple grooves in the tissue.

U.S. Pat. No. 4,069,667 discloses a modification to a HF resectoscope with an insulating extension to the tube surrounding the telescope This modification prevents arcing from the cutting loop to the telescope, with injury to the surgeon.

U.S. Pat. No. 4,362,160 discloses a unipolar cutting loop having a vertical cutting surface which is used in an insulating tube. The tube has triangular or rectangular cut outs which allow the cutting of a wedge shaped meniscus in a joint without touching other tissue. Cutting is achieved by a back and forth motion.

U.S. Pat. No. 5,133,713 discloses a high resistivity loop electrotome heated by high voltage current and which is spun by a motor in an endoscope. Alternatively, a nonelectric knife can be used. The tissue to be resected, for example a prostate, is removed by through multiple shavings by a spinning knife. The size of the loop is fixed.

U.S. Pat. No. 5,437,665 discloses unipolar HF electrodes which are spring mounted and which extend from a sheath, thereby exposing the cutting surfaces. The electrodes form a gap which is used to encircle the point of interest which is dragged through the base of the instrument.

U.S. Pat. No. 5,611,803 a tissue segmentation device in which an excised tissue is placed in a bag containing electrodes which may be heated. Heating the electrodes results in cutting of the tissue into smaller pieces which may be conveniently removed from the body cavity without enlarging the access hole.

U.S. Pat. No. 5,971,994 discloses a HF loop electrode snare used with a gastroscope whose size is adjustable by drawing the loop into or out of a guide channel or tube. The loop is used to engulf tissue to be resected with application of electrical heating at the end of the cutting action.

U.S. Pat. No. 6,416,513 discloses a configurable electrode instrument for peeling of epithelium of ectocervix. The curved configuration of the cutting surface is altered and adjusted by extending or retracting a distal end of a probe to which one end of the electrode is attached.

None of the prior art discloses the properties of the present invention, that of a laparoscopic electrotome with an adjustable-sized cutting loop which is placed adjacent to the tissue to be resected, the loop electrically heated, and the loop rotated, thereby resecting the desired portion of the tissue, while simultaneously cauterizing the tissue with prevention of excessive bleeding. The resected tissue then is grasped using the electrotome mid removed from the body through a trocar for subsequent pathological examination.

BRIEF SUMMARY OF THE INVENTION

This invention application discloses an electrotome for use in laparoscopic surgery. The electrotome comprises a core rod comprising a core rod shaft and a core rod handle, the shaft having a proximal and a distal end, the handle at the proximal end, an electrical conductor extending from an electric connector in the handle to the distal end, the outer surface of the core rod shaft comprised of an electrically nonconductive material. There also is a tubular conductor comprising a tubular conductor shaft and a tubular conductor handle, the shaft and the handle having a bore, the shaft having, a proximal and a distal end, the handle at the proximal end, an electrical connector near the proximal end, and a physical and electrical connector for a cutting electrode at the distal end, the tubular conductor shaft comprised of an electrically conductive material and the tubular conductor handle comprised of electrically nonconductive material. There also is an outer sheath comprising an outer sheath shaft and an outer sheath handle, the shaft and the handle having a bore, the shaft having a proximal and a distal end, the handle at the proximal end, the outer sheath shaft comprised of an electrically nonconductive material. The tubular conductor is shorter than the core rod, and the outer sheath is longer than the tubular conductor and shorter than the core rod. The core rod, tubular conductor, and outer sheath are coaxial sheath the core rod inserted in the tubular conductor and the tubular conductor inserted in the outer sheath. Finally there is a flexible cutting electrode having a first and a second end, the electrode electrically connected at the first end to the core rod electrical conductor at the distal end of the core rod shaft, the electrode electrically connected at the second end to the tubular connector shaft at the distal end of the tubular connector shaft. The cutting electrode assumes a bow shape when the tubular connector is slid toward the distal end of the core rod, the size and shape of the bow capable of modification by sliding the outer sheath toward the distal or the proximal end of the core rod. Electrical cables attach the electrical connectors of the core rod and tubular conductor to a source of electrical current used to heat the cutting electrode.

Also disclosed is a process of treating tissue by resecting, cutting, or destroying the tissue in laparoscopic surgery using an electrotome comprised of a core rod, tubular conductor, outer sheath, and a cutting electrode which comprises the following steps. Inserting the electrotome into a body cavity, manipulating the electrotome so that the tissue to be treated is adjacent to the core rod, forming a bow in the cutting electrode by movement of the tubular conductor in a distal direction, heating the cutting electrode by application of electrical current to the cutting electrode, rotating the core rod and the tubular conductor causing the cutting electrode to come in contact with the tissue to be treated, ceasing application of electrical current to the cutting electrode, and withdrawing the electrotome from the body cavity. The excised tissue can be removed from the body cavity by trapping the excised tissue between the cutting electrode and the core rod before removing the instrument from the body cavity.

The objective of this disclosure is to provide a laproscopic electrotome capable of treating tissues.

Another objective is to provide a laproscopic electrotome which may be inserted through a small orifice.

Another objective is to provide a laproscopic electrotome capable of trapping excised tissue for removal from a body cavity.

Another objective is to provide a laproscopic electrome for resecting, cutting, or destroying tissues.

Another objective is to provide a laproscopic electrotome which cauterizes the cut tissue with reduction of bleeding.

Another objective is to provide a laproscopic electrotome with a cutting electrode whose effective size and shape may be varied.

A final objective is to provide an electrotome which is easily constructed of inexpensive materials without adverse effect on the environment.

BRIEF DESCRIPTION OF THE SEVERAL VIEWS OF THE DRAWING

FIG. 3 is a plan view of the core rod of the first embodiment electrotome.

FIG. 4 is a plan view of the tubular conductor of the first embodiment electrotome.

FIG. 5 is a plan view of the outer sheath of the first embodiment electrotome.

DETAILED DESCRIPTION OF THE INVENTION

In this patent application the term "laparoscopic surgery" means surgery in a body cavity through a small incision in which instruments are manipulated by the operator using direct vision through the incision with the instruments or indirect vision through another incision. "Electrotome" means a surgical instrument in which a wire electrode having high electrical resistance is heated by electrical current and is used to cut, coagulate, destroy or cauterize tissue. "Proximal" refers to the portions of the instrument outside the body cavity. "Distal" refers to the portions of the instrument which extent within the body cavity.

Figure 1:
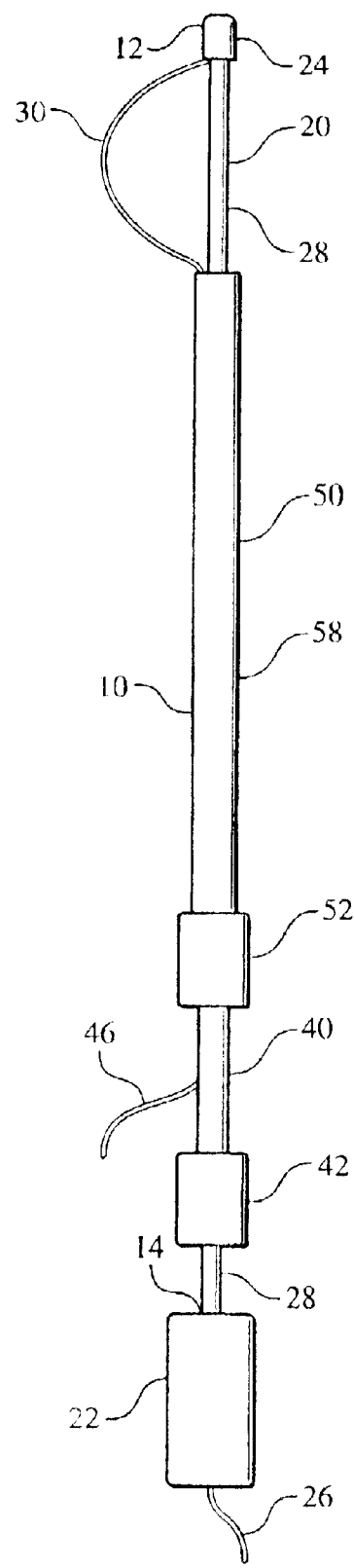
FIG. 1 is a plan view of the first embodiment electrotome.

FIG. 1 is a plan view of the first embodiment electrotome 10. The instrument has a total length of approximately 40 cm is approximately 5 mm, and is designed to fit through incisions of 5 to 15 mm in length. It comprises 4 basic parts, a core rod 20, a tubular conductor 40 into which the core rod 20 is inserted, an outer sheath 50 into which the tubular conductor 40 is inserted, and a cutting electrode 30 which is connected electrically and physically to the core rod 20 and the tubular conductor 40. The core rod 20, tubular conductor 40 and outer sheath 50 are coaxial.

The core rod 20 consists of a core rod shaft 28 which extends the length of the instrument and the core rod handle 22. The core rod shaft 28 has a bore which contains an electrical conductor which extends from the proximal 14 to the distal 12 end in the bar. The core rod shall has an electrically nonconductive coating. An enlarged elongated cylindrical core rod handle 22 is attached to the proximal 14 end of the core rod shall 28. The electrical conductor inside of the core rod shaft 28 is connected to an electrical lead 26 located in the core rod handle 22 which is attached to an electrical generator.

The core rod 20 is slidingly inserted into a tubular conductor 40. The tubular conductor 40 consists of a tubular conductor shaft 48 and tubular conductor handle 42. The tubular conductor shaft 48 is comprised of an electrically conductive material. The tubular conductor handle 42 is an elongated cylindrical tubular structure comprised of electrically nonconductive material. The tubular conductor shaft 48 is connected to a tubular conductor lead 46 which is attached to an electrical generator. The tubular conductor shaft 48 has a connector (44 in FIG. 2) at the distal end (47 in FIG. 2) for making electrical and physical connection with the second end (34 in FIG. 2) of the cutting electrode 30.

The tubular conductor 40 is slidingly inserted into a sheath 50. The sheath 50 consists of a tubular sheath shaft 58 and sheath handle 52. The sheath shaft 58 is comprised of an electrically nonconductive material. The shaft handle 52 is an elongated tubular structure comprised of electrically nonconductive material.

The cutting electrode 30 is electrically and physically connected at a first end to the core rod shaft 28 interior by a connector 24 at the distal end 14 of the core rod shaft 28. The cutting electrode is physically and electrically connected by a connector (44 in FIG. 2) at a second end (34 in FIG. 2) to the distal end (47 in FIG. 2) of the tubular conductor shaft 48. Application of electrical current to the instrument through the core rod electrical lead 26 and the tubular conductor lead 16 therefore passes the current through the cutting electrode 30, causing it to heat.

The cutting electrode preferably is comprised of a flexible, resilient, wire having a substantially circular cross-section or a flat ribbon-like filament of metal having high electrical resistance. A preferred electrode material is NICHROME resistance wire. NICHROME is a trademark for resistant-wire manufactured by Driver-Harris Wire Company, Harrison, N.J.

The cutting electrode 30 is caused to lie flat against the core rod shaft 28 by sliding the tubular conductor handle 42 proximally until it butts against the core rod handle 22. The cutting electrode 30 is caused to bow away from the core rod shaft 29 in a hemispheric shape by sliding the tubular conductor handle 42 distally away from the core rod handle 22. The amount of the bow is controlled by the position of the tubular conductor handle 42. The amount of exposure of the bowed electrode 30 is further controlled by the position of the sheath shaft 58, which is controlled by the position of the sheath handle 52. Retraction of the sheath handle 52 to the extreme proximal position provides maximum exposure of the cutting electrode 30, while extension of the sheath handle 52 to the extreme distal position provides minimum exposure of the cutting electrode 30.

Figure 2:
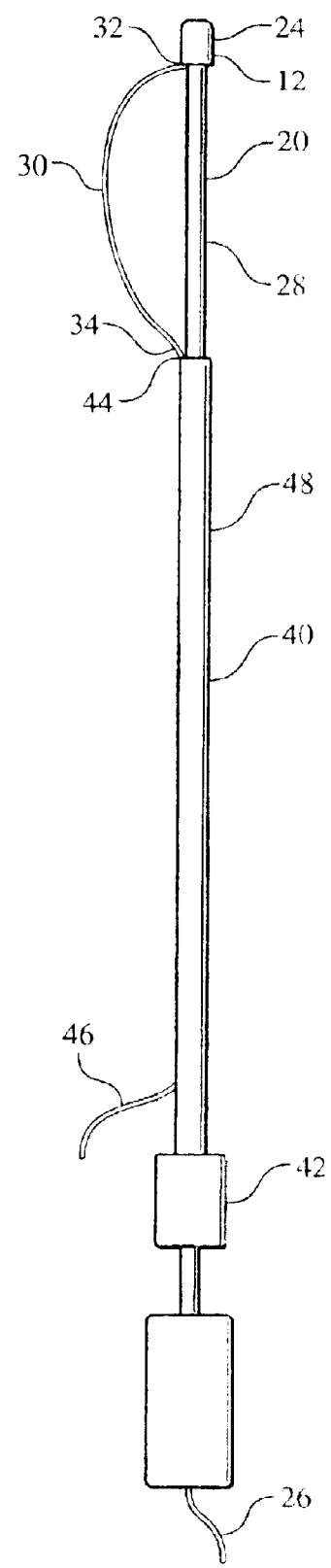
FIG. 2 is a plan view of the first embodiment electrotome with the outer sheath removed.

FIG. 2 is the same as FIG. 1 except the sheath 50 is removed to better show the relationship between core rod 20, cutting electrode 30, and tubular conductor 40. The first end 32 of the cutting electrode 30 is connected to the distal end 12 of the core rod shaft 28 by a core rod connector 24. The second end 34 is connected to the distal end of the tubular connector shaft 48 by a tubular shaft connector 44.

FIG. 3 is a plan view of the core rod 20 of the first embodiment electrotome. Visible in FIG. 3 are the core rod shaft 28 and core rod handle 22 attached at the proximal end 14 of the core rod shade 28. The electrical lead 26 which leads to the electrical generator is shown extending from the core rod handle 22. At the distal end 12 of the core rod shaft 28 a connector 24 makes electrical and physical connection between the conductive core of the core rod shaft 28 and a first end 32 of the cutting electrode 30. The connection to the second end 34 is not shown in FIG. 3.

FIG. 4 is a plan view of the tubular conductor 40 of the first embodiment electrotome. Visible in FIG. 4 is the electrical conductive tubular connector shaft 48, with a connector 44 which provides physical and electrical connection between the tubular connector shaft 48 and the second end 34 of the cutting electrode 30 (shown in FIG. 3) located at the distal 47 end of the tubular connector shaft 48. The tubular connector handle 42 is shown at the proximal 49 end of the tubular connector shaft 48. Also shown is the connector 46 which provides electrical connection between the tubular connector shaft 48 and the source of electrical current.

FIG. 5 is a plan view of the outer sheath 50. Visible in FIG. 5 is the outer sheath shaft 58, the distal end 57 of the outer sheath shaft 58, and the outer sheath shall handle 52 located at the proximal end 59 of the outer sheath shaft 58.

Figure 6A:
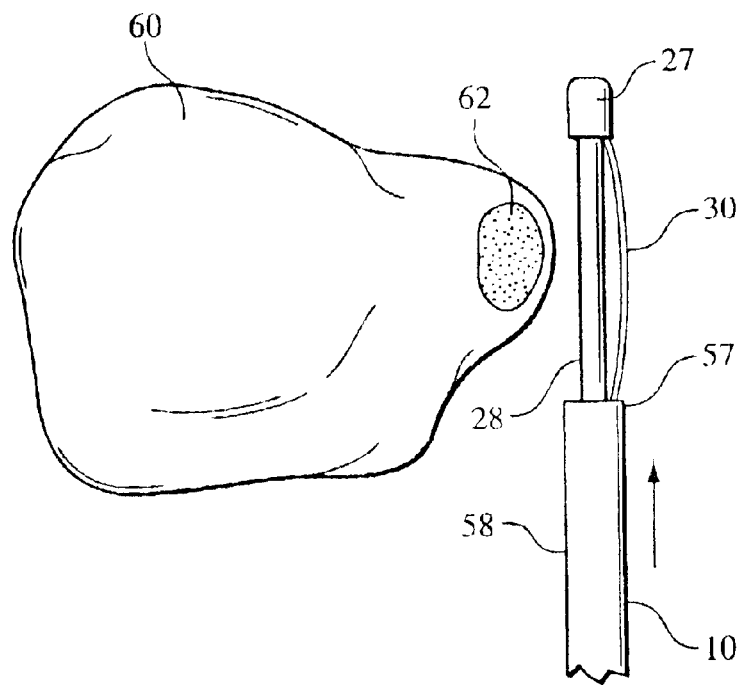
FIG. 6A is a diagrammatic representation of the first embodiment electrotome after insertion through a trochar into a body cavity adjacent to a diseased organ.

FIG. 6A is a diagrammatic representation of the first embodiment electrotome 10 after insertion through a trocar into a body cavity adjacent to a diseased organ 60. A lesion 62 is located on the top of the organ 60. The electrotome 10 is inserted into the body cavity with the cutting electrode 30 adjacent to the core rod shaft 28. The connector 27 which connects the core rod shaft 28 and cutting electrode 30 also is shown in FIG. 6A. The cutting electrode 30 extends beyond the distal end 57 of the outer sheath shaft 58. The arrow indicates the insertion of the electrotome into a body cavity and its manipulation into proximity with a diseased organ.

Figure 6B:
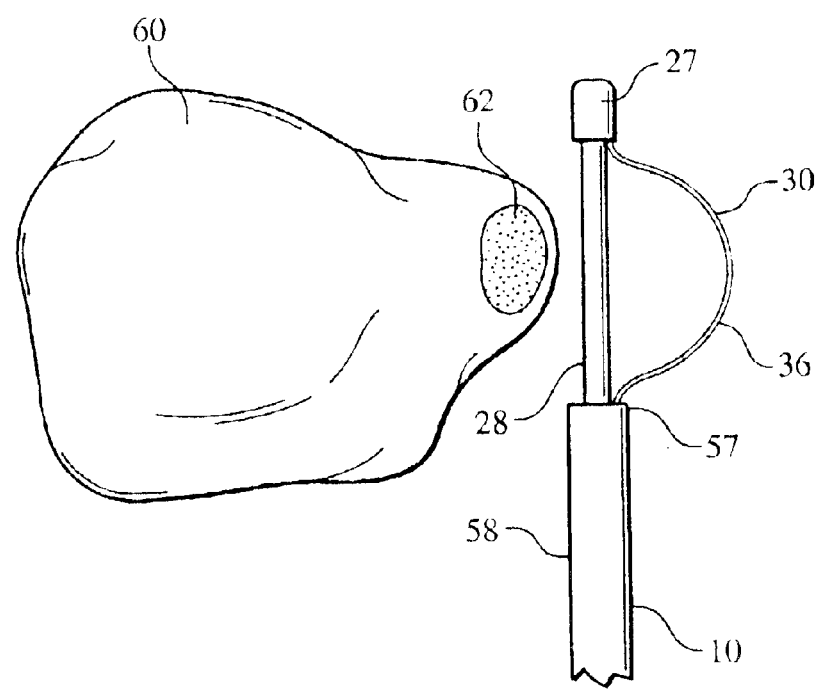
FIG. 6B shows extension of the cutting electrode forming a loop.

FIG. 6B is the same as FIG. 6A except that the operator has moved the tubular conductor handle (not shown in FIG. 6B) in a distal direction causing the cutting electrode 30 to form a bow 36. The outer sheath handle (not shown in FIG. 6B) also has been moved in a distal direction causing the distal end 57 of the outer sheath shaft 58 to shape and limit the size of the bow 36 to the appropriate size and shape for resection of the lesion on the diseased organ.

Figure 6C:
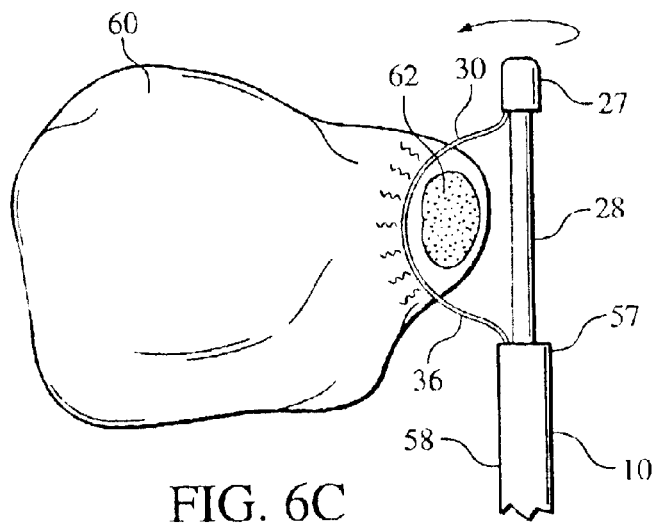
FIG. 6C shows rotation of the core rod along with heating of the cutting electrode causing resection of a portion of the diseased organ.

FIG. 6C is the same as FIG. 6B except that the operator has applied electrical current to the cutting electrode causing the electrode to reach an operating temperature. The operator also has rotated the core rod handle and the tubular conductor handle (not shown in FIG. 6C) in a counterclockwise direction, causing the heated cutting electrode bow 36 to pass into and through the portion of the diseased organ 60 containing the lesion 62.

Figure 6D:
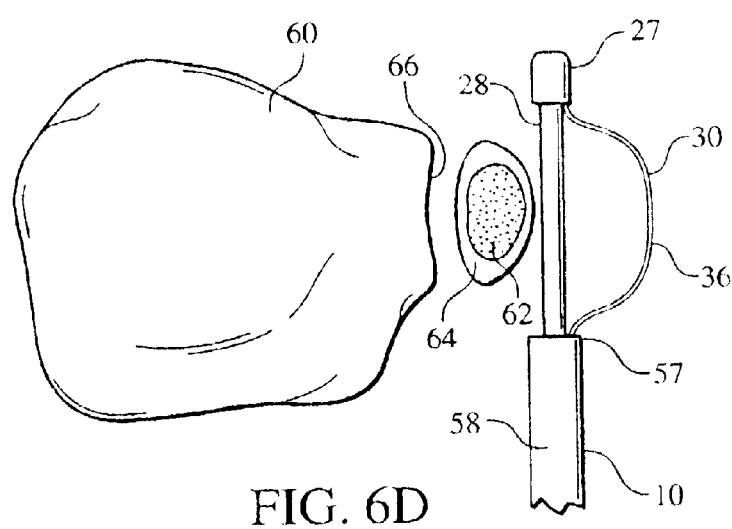
FIG. 6D shows displacement of the resected portion of the diseased organ.

FIG. 6D is the same as FIG. 6C except the rotation of the heated cutting electrode bow 36 through the diseased organ 60 has been completed, resulting in resection of the portion 64 of the diseased organ 60 containing the lesion 62. The surface 66 of the diseased organ 60 has been cauterized by the heated electrode and bleeding is minimized. When the resection is completed the operator turns off the electrical current to the cutting electrode 30. The operator also has moved the tubular conductor handle (not shown in FIG. 6D) in a proximal direction, reducing the size of the cutting electrode bow 36.

Figure 6E:
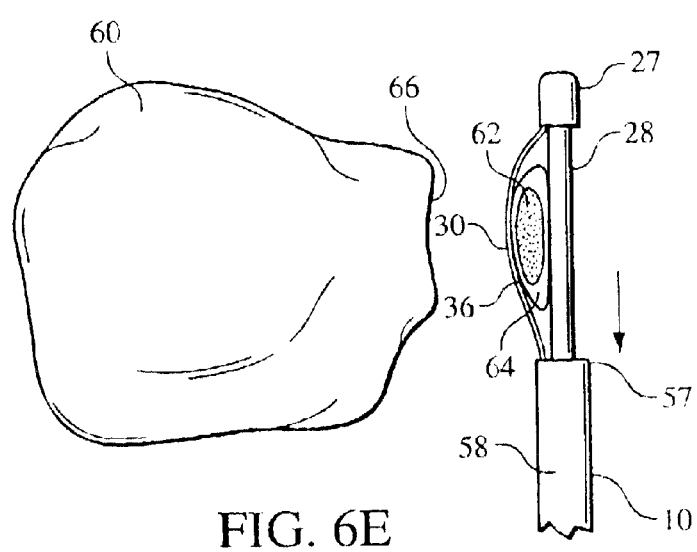
FIG. 6E shows capture of the resected portion of the diseased organ between the cutting electrode and core rod.

FIG. 6E is the same as FIG. 6D except the resected portion 66 of the diseased organ 60 bearing the lesion has been trapped between the core rod shaft 28 and the cutting electrode 30 by a proximal movement of the tubular connector handle (not shown in FIG. 6E) causing reduction of the cutting electrode bow 36. The distal end 57 of the outer sheath shaft 58 has been moved in a distal direction thereby further compressing the cutting electrode 30 against the core rod shaft 28. The electrotome 10 with tripped tissue specimen 64 is then withdrawn from the body cavity, as indicated by the arrow.

Any suitable source of electrical current may be used with the electrotome of this invention. A preferred source is a ValleylabForce Fx Electrosurgical (Generator manufactured by Valleylab, Boulder, Colo. This generator provides, for cutting purposes, 2,500 volts from the highest positive to lowest negative voltage. It has a maximum of 3,000 watts, and typically is used at less than 100 watts. The current is at a frequency of 400–500 kilohertz. The cutting use is used to sever tissue. For coagulation purposes, the generator provides 5,000 to 7,000 peak volts from highest positive to lowest negative voltage. It has a maximum of 120 watts, and typically is used at less than 100 watts. The coagulation use is used to coagulate blood and destroy tissue without a cutting effect.

In use, the electrotome is inserted through a trocar into a body cavity with the tubular conductor handle in the proximal position, causing the cutting electrode to be flattened against the core rod shaft. The portion of the core rod shaft with adjacent cutting electrode is manipulated until it is adjacent to the diseased portion or lesion on an organ, or any other tissue destined to be resected. The lesion may be located on the relative top, side, or bottom of the organ; it is necessary only that the distal end of the core rod with attached cutting electrode be manipulated to be adjacent to the lesion. The surgeon then advances the tubular connector handle in a distal direction, causing the cutting electrode to bow away from the core shaft. The amount of extension of the bowed electrode is further controlled by the position of the distal end of the outer sheath, which is controlled by the outer sheath handle. Movement of the outer sheath handle and distal end of the outer sheath in a distal direction causes the outer sheath to compress and cover the proximal portion of the cutting electrode, causing a reduction of the exposed length of the bowed electrode. Retraction of the outer sheath handle and distal end of the outer sheath in a proximal direction uncovers the proximal portion of the cutting electrode, causing an increase in the exposed length of the bowed electrode.

After the inner core, tubular connector, and outer sheath handles have been manipulated so the cutting electrode has adequate bow and is adjacent to the lesion or other tissue to be resected, an electric current is applied to the electrotome and cutting electrode from the electrical current source. The core rod handle is rotated in a clockwise or counterclockwise direction, causing the bowed cutting electrode to rotate about the inner core with cutting and cauterizing of the tissue. The electrical current is interrupted after the cutting is completed.

After resection, the tissue of interest may be removed from the body cavity by manipulating the core rod, tubular connector, and outer sheath handles in order to capture the tissue between the core rod and the cutting electrode. The electrotome may then be withdrawn from the body cavity. Alternatively, the resected tissue may be grasped and removed by other instruments and the electrotome withdrawn from the body cavity after the bow in the cutting electrode is removed and the cutting electrode flat against the core rod.

EXAMPLE 1

An approximately 23 kg Landrace Yorkshire pig was anesthetized using isofluorane anesthetic administered through general tracheal entubulation. Peritoneal access was obtained using standard laparoscopic ports and the peritoneal cavity inflated The electrotome of this invention was inserted through a trocar and placed near a kidney. A loop was formed in the cutting electrode by distal extension of the tubular conductor. Electrical current was applied to the electrotome, heating the loop, and the handle of the core rod was rotated in a counterclockwise motion, causing the heated loop to resect a wedge of kidney tissue of approximately 3 cm by 3 cm. Cauterization of the cut surface of the kidney occurred immediately with very little bleeding. The loop was allowed to cool and the resected portion of the kidney was grasped between the cutting electrode and the core rod by a proximal movement of the tubular conductor. The electrotome and retained kidney portion was then removed from the peritoneal cavity through the trocar.

It will be apparent to those skilled in the art that the examples and embodiments described herein are by way of illustration and not of limitation, and that other examples may be used without departing from the spirit and scope of the present invention, as set forth in the appended claims.

What is claimed is:

1. An electrotome for use in laparoscopic surgery comprising:
   a core rod comprising a core rod shaft and a core rod handle, the shaft having a proximal and a distal end, the handle at the proximal end, an electrical conductor extending from an electric connector in the handle to the distal end, the outer surface of the core rod shaft comprised of an electrically nonconductive material,
   a tubular conductor comprising a tubular conductor shaft and a tubular conductor handle, the shaft and the handle having a bore, the shaft having a proximal and a distal end, the handle at the proximal end, an electrical connector near the proximal end, and a physical and electrical connector for a cutting electrode at the distal end, the tubular conductor shaft comprised of an electrically conductive material, the tubular conductor handle comprised of electrically nonconductive material,
   an outer sheath comprising an outer sheath shaft and an outer sheath handle, the shaft and the handle having a bore, the shaft having a proximal and a distal end, the handle at the proximal end, the outer sheath shaft comprised of an electrically nonconductive material, the tubular conductor shorter than the core rod, the outer sheath longer than the tubular conductor, and the outer sheath shorter than the core rod,
   the core rod, tubular conductor, and outer sheath coaxial with the core rod inserted in the tubular conductor and the tubular conductor inserted in the outer sheath,
   a flexible cutting electrode having a first and a second end, the electrode electrically connected at the first end to the core rod electrical conductor at the distal end of the core rod shaft, the electrode electrically connected at the second end to the tubular connector shaft at the distal end of the tubular connector shaft,
   the cutting electrode assuming a bow shape when the tubular conductor is slid toward the distal end of the core rod,
   the size and shape of the bow capable of modification by sliding the outer sheath toward the distal or the proximal end of the core rod, and
   electrical cables attaching the electrical connectors of the core rod and tubular conductor to a source of electrical current for heating the cutting electrode.

2. The electrotome of claim 1 wherein the core rod shaft has a bore and the electrical conductor extending from an electric connector in the handle to the distal end of the core rod shaft is in the bore.

3. The electrotome of claim 1 wherein the core rod handle is cylindrical and is comprised of electrically nonconductive material.

4. The electrotome of claim 1 wherein the tubular conductor handle is cylindrical and is comprised of electrically nonconductive material.

5. The electrotome of claim 1 wherein the outer shaft handle is cylindrical and is comprised of electrically nonconductive material.

6. The electrotome of claim 1 wherein the cutting electrode is a flat ribbon-like filament.

7. The electrotome of claim 1 wherein the cutting electrode is a wire having a substantially circular cross section.

8. The electrotome of claim 1 wherein the cutting electrode is comprised of NICHROME.

9. The process of treating tissue by resecting, cutting, or destroying the tissue in laparoscopic surgery using an electrotome comprised of a core rod, tubular conductor, outer sheath, and a cutting electrode comprising the steps:
   1. inserting the electrotome into a body cavity,
   2. manipulating the electrotome so that the tissue to be treated is adjacent to the core rod,
   3. forming a bow in the cutting electrode by movement of the tubular conductor in a distal direction,
   4. heating the cutting electrode by application of electrical current to the cutting electrode,
   5. rotating the core rod and the tubular conductor causing the cutting electrode to come in contact with the tissue to be treated,
   6. ceasing application of electrical current to the cutting electrode, and
   7. withdrawing the electrotome from the body cavity.

10. The process of claim 9 further comprising the step following step 6 and before step 7:
   6A. trapping the treated tissue between the cutting electrode and the core rod.

11. The process of claim 9 wherein the electrotome is inserted into the body cavity through a trocar.

12. The process of claim 9 wherein the treated tissue is resected.

13. The process of claim 9 wherein the tissue to be treated is a kidney.

14. The process of claim 9 wherein the treatment of the tissue is resection of a portion of the tissue having a lesion.

15. The process of claim 9 wherein the treatment of the tissue is resection of a cancerous portion of a kidney.

* * * * *